United States Patent [19]

Hayashi et al.

[11] 4,232,009
[45] Nov. 4, 1980

[54] ω-HALO-PGI₂ ANALOGUES

[75] Inventors: Masaki Hayashi, Takatsuki; Yoshinobu Arai, Toyonaka; Shuichi Ohuchida, Kyoto; Shinsuke Hashimoto, Nishinomiya, all of Japan

[73] Assignee: ONO Pharmaceutical Co. Ltd., Osaka, Japan

[21] Appl. No.: 14,082

[22] Filed: Feb. 22, 1979

[30] Foreign Application Priority Data

Mar. 1, 1978 [JP] Japan ............................ 53/022150

[51] Int. Cl.³ .................... A61K 31/70; A61K 31/58; C07D 307/935
[52] U.S. Cl. .................................. 424/180; 424/285; 536/46; 536/103; 542/426; 542/429; 260/346.22; 260/346.73
[58] Field of Search .................. 260/346.22, 346.73; 542/429, 426; 424/285, 180; 536/43, 103

[56] References Cited

PUBLICATIONS

Chem. and Engineering News, Dec. 1976, p. 17.

Primary Examiner—Henry R. Jiles
Assistant Examiner—Bernard Dentz
Attorney, Agent, or Firm—Stevens, Davis, Miller & Mosher

[57] ABSTRACT

Prostaglandin I₂ analogues of the formula:

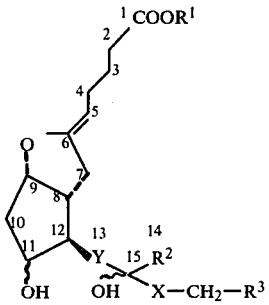

[wherein Y represents ethylene or trans-vinylene, $R^1$ represents hydrogen, alkyl of 1 to 12 carbon atoms, aralkyl of 7 to 12 carbon atoms, cycloalkyl of 4 to 7 carbon atoms optionally substituted by at least one alkyl group containing from 1 to 4 carbon atoms, phenyl unsubstituted or substituted by at least one chlorine atom, trifluoromethyl group, alkyl group containing from 1 to 4 carbon atoms or phenyl group, a —$C_mH_{2-m}COOR^4$ group (wherein m is an integer from 1 to 12 and $R^4$ represents alkyl of 1 to 4 carbon atoms), a $C_nH_{2n}OR^5$ group (wherein n is an integer from 2 to 12 and $R^5$ represents hydrogen or alkyl of 1 to 4 carbon atoms), or a

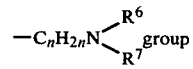

(wherein n is as hereinbefore defined and $R^6$ and $R^7$ each represent alkyl of 1 to 4 carbon atoms), $R^2$ represents hydrogen, methyl or ethyl, X represents a —$C_pH_{2p}$—group (wherein p is an integer from 2 to 8) or a

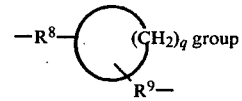

(wherein $R^8$ represents a single bond, or alkylene of 1 to 4 carbon atoms, $R^9$ represents a single bond or alkylene of 1 to 8 carbon atoms, and q is an integer from 3 to 6), $R^3$ represents chlorine or fluorine, the wavy line attached to the carbon atoms in positions 11 and 15 represents α- or β-configuration or mixtures thereof, and the double bond between $C_5$-$C_6$ is Z] and cyclodextrin clathrates thereof and, when appropriate non-toxic salts, including acid addition salts, thereof, are new compounds possessing prostaglandin-like activity.

19 Claims, No Drawings

ω-HALO-PGI₂ ANALOGUES

DESCRIPTION

This invention relates to new prostaglandin I₂ (PGI₂) analogues, to a process for their preparation and to pharmaceutical compositions containing them.

PGI₂ is a physiologically active natural substance having the following formula:

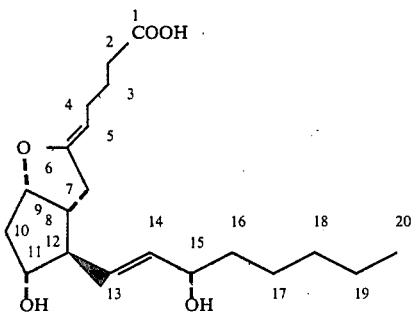

I and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI₂ can be prepared by incubation of prostaglandin G₂ (PGG₂) or prostaglandin H₂ (PGH₂) with microsomal fractions prepared from thoracic aorta of swine, mesenteric artery of swine, rabbit aorta or the stomach fundus of rats. PGI₂ has a relaxing activity on the artery, which is peculiar to the artery and which does not operate on other smooth muscle. Furthermore, PGI₂ strongly inhibits arachidonic acid-induced blood platelet aggregation of the human.

Taking into consideration that thromboxane A₂ prepared by incubation of PGG₂ or PGH₂ with blood platelet microsome has a contracting activity on the artery and an aggregating activity on blood platelets, the properties of PGI₂ heretofore mentioned show that PGI₂ fulfills a very important physiological part in a living body. PGI₂ may be useful in the treatment of arteriosclerosis, cardiac failure or thrombosis.

Widespread investigations have been carried out in order to discover inter alia new products possessing the pharmacological properties of the 'natural' PGI₂ or one or more of such properties to an enhanced degree, or hitherto unknown pharmacological properties. As a result of extensive research and experimentation it has now been discovered that by replacing one of the hydrogen atoms at the end of the n-pentyl group linked to the 15-position of PGI₂, and certain analogues thereof in which the n-pentyl group is itself replaced by another alkyl group which optionally includes a cycloalkyl ring, by a halogen atom, the pharmacological properties of the 'natural' PGI₂ are, in some aspects of its activities, improved or modified.

The present invention accordingly provides new prostaglandin I₂ analogues of the general formula:

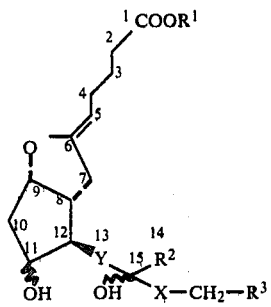

II

[wherein Y represents ethylene (i.e. —CH₂CH₂—) or, preferably, trans-vinylene

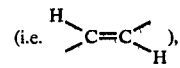

(i.e. $\underset{\diagup}{H}C=C\underset{H}{\diagdown}$ ),

R¹ represents a hydrogen atom, a straight- or branched-chain alkyl group containing from 1 to 12, and preferably from 1 to 4 carbon atoms, an aralkyl group containing from 7 to 12 carbon atoms, a cycloalkyl group containing from 4 to 7 carbon atoms unsubstituted or substituted by at least one straight- or branched-chain alkyl group containing from 1 to 4 carbon atoms, a phenyl group unsubstituted or substituted by at least one chlorine atom, trifluoromethyl group, straight- or branched-chain alkyl group containing from 1 to 4 carbon atoms or phenyl group, a —C$_m$H$_{2m}$COOR⁴ group (wherein m represents an integer of from 1 to 12 and R⁴ represents a straight- or branched-chain alkyl group containing from 1 to 4 carbon atoms), a —C$_n$H$_{2n}$OR⁵ group (wherein n represents an integer of from 2 to 12 and R⁵ represents a hydrogen atom or a straight- or branched-chain alkyl group containing from 1 to 4 carbon atoms), or a

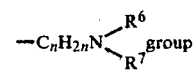

(wherein n is as hereinbefore defined and R⁶ and R⁷, which may be the same or different, each represent a straight- or branched-chain alkyl group containing from 1 to 4 carbon atoms), R² represents a methyl or ethyl group, or preferably a hydrogen atom, X represents a straight or branched chain —C$_p$H$_{2p}$-group (wherein p represents an integer of from 2 to 8) or a

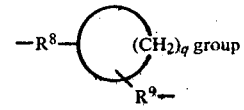

(wherein R⁸ represents a single bond, or a straight- or branched-chain alkylene group containing from 1 to 4 carbon atoms, R⁹ represents a single bond or a straight- or branched-chain alkylene group containing from 1 to 8 carbon atoms, and q represents an integer of from 3 to 6), R³ represents a chlorine or fluorine atom, the wavy line attached to the carbon atoms in positions 11 and 15 represents α- or β-configuration (i.e. S- or R-configuration) or mixtures thereof, and the double bond between C₅-C₆ is Z] and cyclodextrin clathrates of such acids and esters and, when $R^1$ represents a hydrogen atom, non-toxic (e.g. sodium) salts thereof and, when $R^1$ represents a

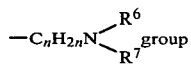

in which n, $R^6$ and $R^7$ are as hereinbefore defined, non-toxic acid addition salts thereof. Preferably the hydroxy groups attached to the C-11 and C-15 carbon atoms of formula II are in α-configuration. It is to be understood that in the

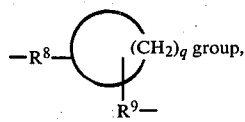

$R^9$ may be attached to any of the carbon atoms of the cycloalkyl ring including the carbon atom (not depicted) which is attached to $R^8$.

The present invention is concerned with all compounds of general formula II in the 'natural' form or its enantiomeric form, or mixtures thereof, more particularly the racemic form consisting of equimolecular mixtures of natural and its enantiomeric form.

As will be apparent to those skilled in the art, the compounds depicted in general formula II have at least five centres of chirality, these five centres of chirality being at the C-8, C-9, C-11, C-12 and C-15 carbon atoms. Still further centres of chirality may occur when $R^1$ is a branched-chain alkyl group or $C_mH_{2m}$, $C_nH_{2n}$, $C_pH_{2p}$, $R^8$ or $R^9$ is a branched-chain alkylene group. The presence of chirality leads, as is well known, to the existence of isomerism. However, the compounds of general formula II all have such a configuration that the side-chains attached to the ring carbon atoms in the positions identified as 8 and 12 are trans with respect to each other. Accordingly, all isomers of general formula II and mixtures thereof, which have those side-chains attached to the ring carbon atoms in positions 8 and 12 in the trans configuration and have hydroxy groups as depicted in the 11- and 15-positions are to be considered within the scope of formula II.

Examples of the straight- or branched-chain alkyl group containing from 1 to 12 carbon atoms represented by $R^1$ are methyl, ethyl, propyl, butyl, pentyl, hexyl, heptyl, octyl, nonyl, decyl, undecyl and dodecyl and their isomers.

Examples of the aralkyl group containing from 7 to 12 carbon atoms represented by $R^1$ are benzyl, 1-phenylethyl, 2-phenylethyl, 3-phenylbutyl, 4-phenylbutyl, 1-(2-naphthyl)ethyl and 2-(1-naphthyl)ethyl.

Examples of the cycloalkyl group containing from 4 to 7 carbon atoms unsubstituted or substituted by at least one straight- or branched-chain alkyl group containing from 1 to 4 carbon atoms represented by $R^1$ are cyclobutyl, 1-propylcyclobutyl, 1-butylcyclobutyl, 2-methylcyclobutyl, 3-ethylcyclobutyl, 3-propylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, 2,6-dimethyl-4-propylcyclohexyl and cycloheptyl.

Examples of the phenyl group unsubstituted or substituted by at least one chlorine atom, trifluoromethyl group, straight- or branched-chain alkyl group containing from 1 to 4 carbon atoms or phenyl group represented by $R^1$ are phenyl, 2-chlorophenyl, 3-chlorophenyl, 4-chlorophenyl, 2,4-dichlorophenyl, 2,4,6-trichlorophenyl, 2-tolyl, 3-tolyl, 4-tolyl, 4-ethylphenyl, 4-tert-butylphenyl, 4-sec-butylphenyl, 3-trifluoromethylphenyl and 4-biphenyl.

$R^1$ preferably represents a straight- or branched-chain alkyl group containing from 1 to 4 carbon atoms, e.g. methyl.

Examples of the $C_mH_{2m}$ and $C_nH_{2n}$ moieties of the $C_mH_{2m}COOR^4$, $C_nH_{2n}OR^5$ and

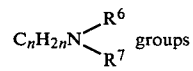

represented by $R^1$, are methylene (when m in the $C_mH_{2m}$ moiety is 1), ethylene, trimethylene, tetramethylene, pentamethylene, hexamethylene, heptamethylene, octamethylene, nonamethylene, decamethylene, undecamethylene, dodecamethylene and their isomers.

Examples of the straight- or branched-chain alkyl group containing from 1 to 4 carbon atoms represented by $R^4$, $R^5$, $R^6$ and $R^7$, are methyl, ethyl, propyl, isopropyl, butyl, isobutyl, sec-butyl and tert-butyl.

Examples of the alkylene group containing from 2 to 8 carbon atoms represented by $C_pH_{2p}$, are ethylene, trimethylene, tetramethylene, pentamethylene, hexamethylene, heptamethylene, octamethylene, and their isomers.

Examples of the

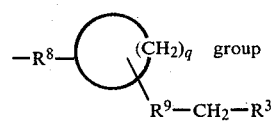

represented by —X—CH$_2$—R$^3$ are 1-(3-chloropropyl)cyclobutyl, 1-(4-chlorobutyl)cyclobutyl, 1-(5-chloropentyl)cyclobutyl, 1-(6-chlorohexyl)cyclobutyl, 2-(3-chloropropyl)cyclobutyl, 2-(3-chloroethyl)cyclobutyl, 3-(3-chloropropyl)cyclobutyl, 3-chloromethylcyclopentyl, 3-(2-chloroethyl)cyclopentyl, 3-(3-chloropropyl)cyclopentyl, 3-(4-chlorobutyl)cyclopentyl, 3-chloromethylcyclopentylmethyl, 3-(2-chloroethyl)cyclopentylmethyl, 4-chloromethylcyclohexyl, 4-(2-chloroethyl)cyclohexyl, 4-(3-chloropropyl)cyclohexyl, 3-chloromethylcyclohexylmethyl, 3-(2-chloroethyl)cyclohexylmethyl, 4-chloromethylcyclohexylmethyl, 4-(2-chloroethyl)cyclohexylmethyl, and the corresponding groups in which the chlorine atom is replaced by a fluorine atom; 1-(4-fluorobutyl)cyclobutyl and 3-(2-chloroethyl)cyclopentyl are preferred.

The symbol X preferably represents a tetramethylene group unsubstituted or substituted by a methyl group or a

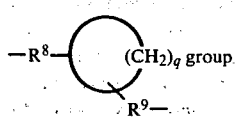

in which $R^8$ represents a single bond, q represents 3 or 4 and $R^9$ represents a straight-chain alkylene group containing from 1 to 3 carbon atoms.

According to a feature of the present invention, the prostaglandin $I_2$ analogues of general formula II, wherein the various symbols are as hereinbefore defined, are prepared by dehydrohalogenation (i.e. dehydrobromination or dehydroiodination) of a compound of the general formula:

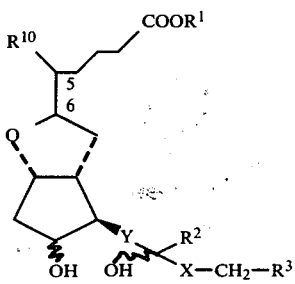

wherein $R^{10}$ represents a bromine or iodine atom, the absolute configurations of $C_5$ and $C_6$ are (5S,6S) or (5R,6R) or a mixture thereof (5RS,6RS), and the other symbols are as hereinbefore defined.

The dehydrohalogenation may be carried out with a known dehydrohalogenation reagent, for example, (1) when $R^{10}$ represents a bromine atom, a bicycloamine such as 1,5-diazabicyclo[5,4,0]undecene-5 (DBU), 1,5-diazabicyclo[4,3,0]-nonene-5 (DBN) or 1,4-diazabicyclo[2,2,2]octane (DABCO), or an alkali metal, e.g. sodium or potassium, alcoholate containing from 1 to 4 carbon atoms, or (2) when $R^{10}$ represents an iodine atom, a bicycloamine such as DBU, DBN or DABCO, or an alkali metal, e.g. sodium or potassium, alcoholate containing from 1 to 4 carbon atoms, superoxide, carbonate, hydroxide, benzoate, acetate, trifluoroacetate or bicarbonate, or silver acetate, or tetramethylammonium superoxide. The reaction may be carried out at a temperature from ambient to 110° C., preferably at a temperature from ambient to 80° C., and (1) when the reagent is a bicycloamine, optionally in the presence of an inert organic solvent, preferably in the absence of an inert organic solvent or in the presence of toluene or benzene, or (2) when the reagent is other than a bicycloamine, in the presence of an inert organic solvent, e.g. an alkanol containing from 1 to 4 carbon atoms, such as methanol or ethanol, or N,N-dimethylformamide.

Compounds of general formula III, wherein the various symbols are as hereinbefore defined, may be prepared by the hydrolysis to a hydroxy group of the group $OR^{11}$ and, when $R^{12}$ is other than a hydrogen atom, of the group $OR^{12}$ of a compound of the general formula:

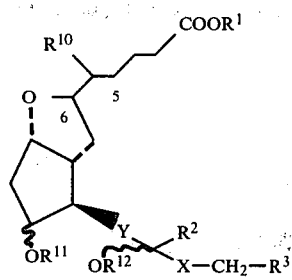

wherein $R^{11}$ represents a tetrahydropyran-2-yl or tetrahydrofuran-2-yl group, each such group being unsubstituted or substituted by at least one alkyl group, or a 1-ethoxyethyl group, $R^{12}$ represents a hydrogen atom, a tetrahydropyran-2-yl or tetrahydrofuran-2-yl group, each such group being unsubstituted or substituted by at least one alkyl group, or a 1-ethoxyethyl group, the absolute configurations of $C_5$ and $C_6$ are (5R,6R) or (5S,6S) or a mixture thereof, and the other symbols are as hereinbefore defined.

The groups $OR^{11}$ and $OR^{12}$ (when $R^{12}$ is other than a hydrogen atom) of the compounds of general formula IV may be converted to hydroxy groups by mild acidic hydrolysis (1) with an aqueous solution of an organic acid such as acetic acid, propionic acid, oxalic acid, or p-toluenesulphonic acid, or an aqueous solution of an inorganic acid such as hydrochloric, sulphuric or phosphoric acid, advantageously in the presence of an inert organic solvent miscible with water, e.g. a lower alkanol such as methanol or ethanol, preferably methanol, or an ether such as 1,2-dimethoxyethane, dioxan, or tetrahydrofuran (preferably tetrahydrofuran), at a temperature ranging from ambient to 75° C. (preferably at a temperature from ambient to 45° C.), or (2) with an anhydrous solution of an organic acid such as p-toluenesulfonic acid or trifluoroacetic acid in a lower alkanol such as methanol or ethanol at a temperature ranging from 10° to 45° C. Advantageously the mild acidic hydrolysis may be carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, or a mixture of p-toluenesulphonic acid and methanol.

Compounds of general formulae III and IV, i.e. compounds of the general formula:

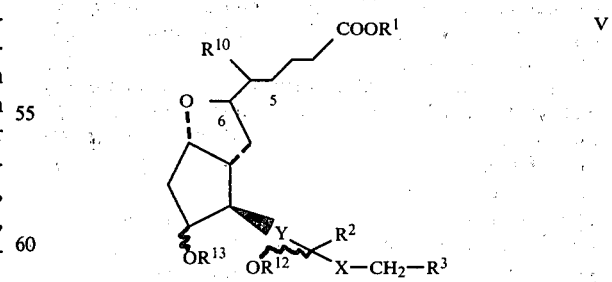

(wherein $R^{13}$ represents a hydrogen atom, a tetrahydropyran-2-yl or tetrahydrofuran-2-yl group, each such group being unsubstituted or substituted by at least one alkyl group, or a 1-ethoxyethyl group, the absolute configurations at $C_5$ and $C_6$ are (5R,6R) or (5S,6S) or a mixture thereof, and the other symbols are as hereinbefore defined), may be prepared by the bromination or iodination, and simultaneous cyclisation, of a compound of the general formula:

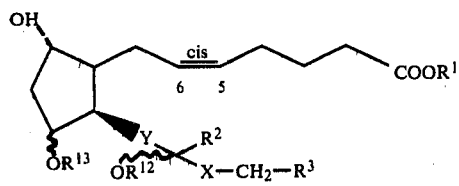

wherein the double bond between $C_5$-$C_6$ is cis and the other symbols are as hereinbefore defined.

The conversion of a compound of general formula VI to a compound of general formula V may be suitably carried out, (1) when $R^{10}$ in the compound of formula V represents a bromine atom, with N-bromosuccinimide or N-bromoacetamide in an aprotic organic solvent, e.g. methylene chloride, chloroform, carbon tetrachloride, diethyl ether, N,N-dimethylformamide or tetrahydrofuran, or a mixture of two or more of them, at a temperature of from $-30°$ to $70°$ C., or (2) when $R^{10}$ in the compound of formula V represents an iodine atom, with (i) iodine in pyridine, (ii) potassium periodate and potassium iodide in aqueous acetic acid, (iii) iodine and potassium iodide in the presence of an alkali metal, e.g. sodium or potassium, carbonate or bicarbonate in water, or (iv) iodine in the presence of an alkali metal, e.g. sodium or potassium, carbonate in an inert organic solvent, e.g. methylene chloride or chloroform, at a temperature of from $0°$ C. to ambient. The product of general formula V, thus obtained, is a mixture of isomers in which the absolute configurations of $C_5$ and $C_6$ are (5R,6R) and (5S,6S). If desired, the mixture may be separated by column, thin layer or high-speed liquid chromatography on silica gel to give each of the isomers. Each isomer or the mixture of isomers may be converted to the desired $PGI_2$ analogues of general formula II as described above, so that it is not necessary to separate the isomers unless such separation is particularly desired.

The methods hereinbefore described for the preparation of $PGI_2$ analogues of general formula II may be represented by the series of reactions depicted schematically below in Scheme A, wherein the various symbols are as hereinbefore defined, the absolute configurations at $C_5$ and $C_6$ in formulae III and IV are (5R,6R) or (5S,6S) or a mixture thereof and the double bond between $C_5$-$C_6$ in formula II is Z.

SCHEME A

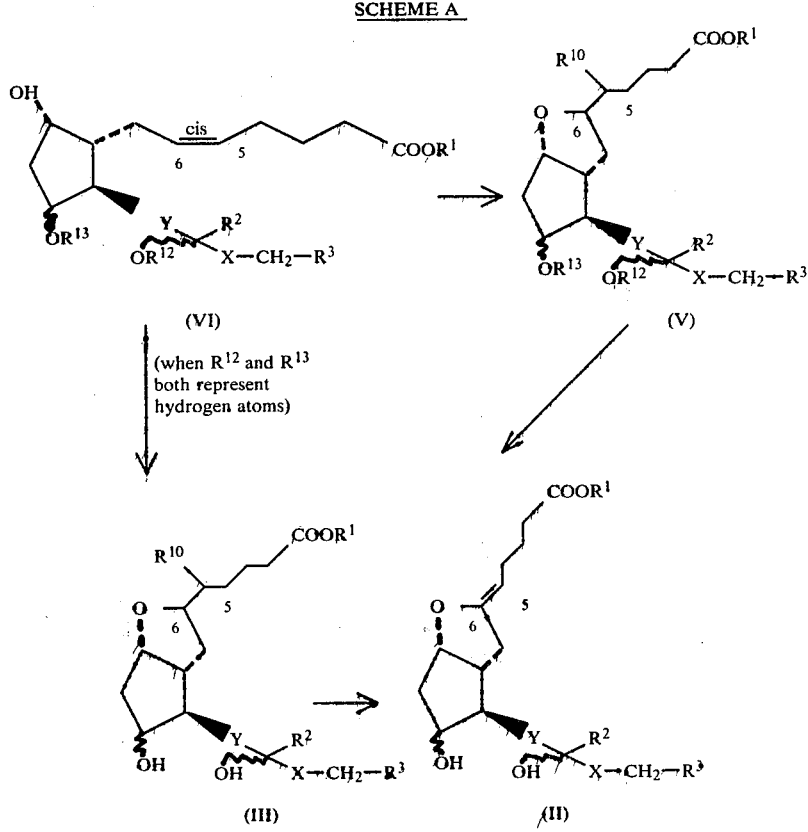

The esters of general formula III, V or VI wherein $R^1$ is other than a hydrogen atom and the other symbols are as hereinbefore defined may be obtained by the esterification, by methods known per se, of the corresponding acids of general formula III, V or VI. By the expression "methods known per se" as used in this specification is meant methods heretofore used or described in the chemical literature. The esterification may be carried out, for example when $R^1$ represents an alkyl group, using (1) a diazoalkane, (2) an alkyl halide, or (3) an N,N-dimethylformamidedialkyl acetal, or when $R^1$ represents a group other than a hydrogen atom, (4) dicyclohexylcarbodiimide (by the procedure described in our Japanese Pat. No. 762305), (5) a pivaloyl halide (by the procedure described in our British Pat. No. 1364125), or (6) an arylsulphonyl or alkylsulphonyl halide (by the procedure described in our British Pat. No. 1362956).

The preparation of esters using a diazoalkane is carried out by reacting the corresponding acid with an appropriate diazoalkane in an inert organic solvent, e.g. diethyl ether, ethyl acetate, methylene chloride or acetone, or a mixture of two or more of them, at a temperature of from −10° C. to ambient, preferably 0° C. The preparation of esters using an alkyl halide is carried out by reacting the corresponding acid with an appropriate alkyl halide, e.g. methyl iodide, (i) in acetone in the presence of a carbonate of an alkali metal, such as potassium carbonate [cf. J. Org. Chem., 34, 3717 (1967)], (ii) in N,N-dimethylacetamide or N,N-dimethylformamide in the presence of a bicarbonate of an alkali metal, such as sodium or potassium bicarbonate [cf. Advan. Org. Chem., 5, 37 (1965)], or (iii) in dimethyl sulphoxide in the presence of calcium oxide [cf. Synthesis, 262 (1972)]. The preparation of esters using an N,N-dimethylformamide-dialkyl acetal is carried out by reacting the corresponding acid with an N,N-dimethylformamide-dialkyl acetal, e.g. N,N-dimethylformamide-dimethyl acetal, in anhydrous benzene [cf. Helv. Chem. Acta., 48, 1746 (1965)]. The preparation of esters using dicyclohexylcarbodiimide is carried out by reacting the corresponding acid with an appropriate alcohol $R^1OH$, wherein $R^1$ is other than a hydrogen atom, in an inert organic solvent such as a halogenated hydrocarbon, e.g. chloroform or methylene chloride, in the presence of a base such as pyridine or picoline, preferably pyridine, at a temperature from 0° C. to ambient. The preparation of esters using a pivaloyl halide, arylsulphonyl halide or alkylsulphonyl halide is carried out by reacting the corresponding acid with a tertiary amine, e.g. triethylamine, or pyridine and a pivaloyl halide (e.g. pivaloyl chloride), arylsulphonyl halide (e.g. benzenesulphonyl chloride or p-toluenesulphonyl chloride) or alkylsulphonyl halide (e.g. methanesulphonyl chloride or ethanesulphonyl chloride) in the presence or absence of an inert organic solvent such as a halogenated hydrocarbon, e.g. chloroform or methylene chloride, or diethyl ether to prepare a mixed acid anhydride, and adding thereto an appropriate alcohol at a temperature from 0° C. to ambient.

Starting materials of general formula VI may be prepared by the methods described in the following patent applications and specifications, or obvious modifications thereof: British Patent Application No. 22090/75, Belgian Specification No. 842113, and British Patent Application No. 29756/78 as published under the Serial No. 2002355A.

In particular, starting materials of general formula VI may be prepared by the synthetic routes described in the abovementioned patent applications, using as a starting material a compound of the general formula:

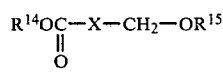

VII wherein $R^{14}$ represents a hydrogen atom or a straight- or branched-chain alkyl group containing from 1 to 4 carbon atoms, $R^{15}$ represents a hydrogen atom, a tetrahydropyran-2-yl or tetrahydrofuran-2-yl group, each such group being unsubstituted or substituted by at least one alkyl group, or a 1-ethoxyethyl group, and X is as hereinbefore defined.

The compounds of general formula VII may be prepared by methods known per se.

For example, the compounds of general formula VII, wherein $R^{14}$ represents a straight- or branched-chain alkyl group containing from 1 to 4 carbon atoms, $R^{15}$ represents a tetrahydropyran-2-yl or tetrahydrofuran-2-yl group, each such group being unsubstituted or substituted by at least one alkyl group, or a 1-ethoxyethyl group, and X is as hereinbefore defined, may be reacted with a lithio derivative of the formula:

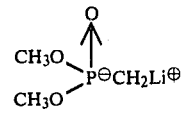

VIII to obtain a compound of the general formula:

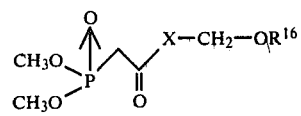

IX (wherein $R^{16}$ represents a tetrahydropyran-2-yl or tetrahydrofuran-2-yl group, each such group being unsubstituted or substituted by at least one alkyl group, or a 1-ethoxyethyl group, and X is as hereinbefore defined), which is reacted with a compound of the general formula:

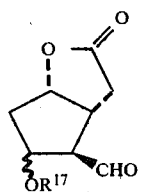

X (wherein $R^{17}$ represents an acetyl group or a p-phenylbenzoyl group) to obtain, via the series of reactions depicted in Scheme B of British Patent Application No. 29756/78 as published under the number 2,002355A, a compound of the general formula:

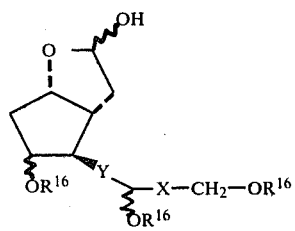

XI wherein the various symbols are as hereinbefore defined.

The compounds of general formula XI may be converted into compounds of general formula VI, wherein $R^1$, $R^2$, $R^{12}$ and $R^{13}$ each represent a hydrogen atom and the other symbols are as hereinbefore defined, by the series of reactions depicted schematically below in Scheme B. Reaction conditions suitable for effecting the reactions depicted are described in the two British and Belgian applications and specifications referred to above. In Scheme B, $R^{18}$ represents an arylsulphonyl group, preferably a p-toluenesulphonyl or benzenesulphonyl group, the other symbols are as hereinbefore defined, and the double bonds in the $C_5$-$C_6$ positions are cis.

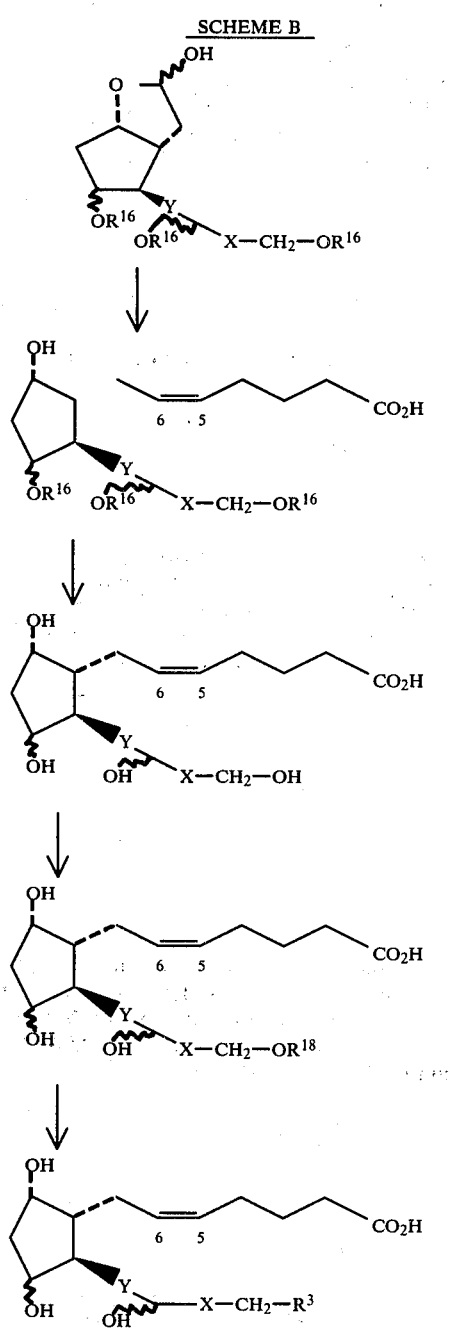

Esters of the prostaglandin $I_2$ analogues of general formula II, wherein $R^1$ represents a straight- or branched-chain alkyl group containing from 1 to 12 carbon atoms and the other symbols are as hereinbefore defined, may be prepared by esterification of the corresponding acid of general formula II wherein $R^1$ represents a hydrogen atom by methods known per se, for example by reaction with the appropriate diazoalkane in an inert organic solvent, e.g. diethyl ether, ethyl acetate, methylene chloride or acetone, or a mixture of two or more of them, at a temperature of from $-10°$ C. to ambient and preferably 0° C.

Cyclodextrin clathrates of the prostaglandin $I_2$ analogues of general formula II may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. $\alpha$-, $\beta$- or $\gamma$-Cyclodextrins or mixtures thereof may be used in the preparation of the cyclodextrin clathrates. Conversion into cyclodextrin clathrates serves to increase the stability of the prostaglandin $I_2$ analogues of general formula II.

Compounds of general formula II wherein $R^1$ represents a hydrogen atom may, if desired, be converted by methods known per se into salts. Preferably the salts are non-toxic salts. By the term 'non-toxic salts', as used in this specification, is meant salts the cations (or in the case of acid addition salts referred to hereinafter the anions) of which are relatively innocuous to the animal organism when used in therapeutic doses so that the beneficial pharmacological properties of the compounds of general formula II are not vitiated by side-effects ascribable to those cations (or anions). Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms. Suitable non-toxic amine salts are, e.g. tetraalkylammonium, such as tetramethylammonium, salts, and other organic amine salts such as methylamine salts, dimethylamine salts, cyclopentylamine salts, benzylamine salts, phenethylamine salts, piperidine salts, monoethanolamine salts, diethanolamine salts, lysine salts or arginine salts.

Salts may be prepared from the acids of general formula II wherein $R^1$ represents a hydrogen atom by methods known per se, for example by reaction of stoichiometric quantities of an acid of general formula II and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

Sodium salts may also be prepared by treatment of an ester of general formula II, wherein $R^1$ represents an alkyl group containing from 1 to 12 carbon atoms and the other symbols are as hereinbefore defined, with one equivalent amount of sodium hydroxide in the presence of an aqueous alkanol containing from 1 to 4 carbon atoms, preferably aqueous methanol, at a temperature of from 0° to 60° C., preferably at ambient temperature.

Prostaglandin analogues of general formula II wherein R¹ represents a group

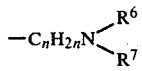

wherein n, R⁶ and R⁷ are as hereinbefore defined may be converted by methods known per se into acid addition salts, which are preferably non-toxic as hereinbefore defined. Suitable acid addition salts are those formed with inorganic acids (such as hydrochlorides and sulphates) and with organic acids (such as acetates, propionates, succinates and benzoates).

The prostaglandin analogues of general formula II and their cyclodextrin clathrates, and when R¹ represents a hydrogen atom, non-toxic salts and, when R¹ represents a

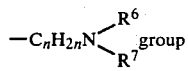

in which n, R⁶ and R⁷ are as hereinbefore defined, non-toxic acid addition salts thereof, possess the valuable pharmacological properties typical of the prostaglandins in a selective fashion, in particular hypotensive activity, inhibitory activity on blood platelet aggregation and stimulatory activity on uterine contraction, and are useful in the treatment of hypertension, in the treatment of disorders of the peripheral circulation, in the prevention and treatment of cerebral thrombosis, myocardial infarction and arteriosclerosis.

For example, in standard laboratory tests, (i) by intravenous administration to the allobarbital anaesthetized dog, (5Z,13E)-(9α,11α,15S)-6,9-epoxy-11,15-dihydroxy-20-chloroprosta-5,13-dienoic acid methyl ester produces a fall in blood pressure of 14 mmHg and 34 mmHg lasting 4 and 5 minutes at the doses of 0.1 and 0.2 μg/kg animal body weight, respectively, (5Z,13E)-(9α,11α,15S,16RS)-6,9-epoxy-11,15-dihydroxy-16-methyl-20-chloroprosta-5,13-dienoic acid methyl ester produces a fall in blood pressure of 20 mmHg and 48 mmHg lasting 11 and 15 minutes at the doses of 0.1 and 0.2 μg/kg animal body weight, respectively, (5Z,13E)-(9α,11α,15S,17R)-6,9-epoxy-11,15-dihydroxy-17-methyl-20-chloroprosta-5,13-dienoic acid methyl ester produces a fall in blood pressure of 10 mmHg lasting 3 minutes at the dose of 100 μg/kg animal body weight, (5Z,13E)-(9α,11α,15R)-6,9-epoxy-11,15-dihydroxy-15-[1-(4-fluorobutyl)cyclobutyl]-16,17,18,19,20-pentanorprosta-5,13-dienoic acid methyl ester produces a fall in blood pressure of 24 mmHg, 40 mmHg and 52 mmHg lasting 8, 20 and 15 minutes at the doses of 1, 2 and 4 μg/kg animal body weight, respectively, and (5Z,13E)-(9α,11α,15S)-6,9-epoxy-11,15-dihydroxy-15-[3-(2-chloroethyl)cyclopentyl]-16,17,18,19,20-pentanorprosta-5,13-dienoic acid methyl ester produces a fall in blood pressure of 22 mmHg, 32 mmHg and 50 mmHg lasting 9, 11 and 15 minutes at the doses of 0.1, 0.2 and 0.4 μg/kg animal body weight, respectively, (ii) (5Z,13E)-(9α,11α,15S)-6,9-epoxy-11,15-dihydroxy-20-chloroprosta-5,13-dienoic acid methyl ester, (5Z,13E)-(9α,11α,15S,16RS)-6,9-epoxy-11,15-dihydroxy-16-methyl-20-chloroprosta-5,13-dienoic acid methyl ester, (5Z,13E)-(9α,11α,15S,17R)-6,9-epoxy-11,15-dihydroxy-17-methyl-20-chloroprosta-5,13-dienoic acid methyl ester, (5Z,13E)-(9α,11α,15R)-6,9-epoxy-11,15-dihydroxy-15-[1-(4-fluorobutyl)cyclobutyl]-16,17,18,19,20-pentanorprosta-5,13-dienoic acid methyl ester and (5Z,13E)-(9α,11α,15S)-6,9-epoxy-11,15-dihydroxy-15-[3-(2-chloroethyl)cyclopentyl]-16,17,18,19,20-pentanorprosta-5,13-dienoic acid methyl ester produce a 50% inhibition of adenosine diphosphate-induced blood platelet aggregation in platelet-rich plasma of rats at the concentrations of $4.0 \times 10^{-3}$, $1.5 \times 10^{-3}$, $3.3 \times 10^{-3}$, $1.8 \times 10^{-2}$ and $2.3 \times 10^{-3}$ μg/ml, respectively, in comparison with controls, and (iii) (5Z,13E)-(9α,11α,15S,16RS)-6,9-epoxy-11,15-dihydroxy-16-methyl-20-chloroprosta-5,13-dienoic acid methyl ester and (5Z,13E)-(9α,11α,15R)-6,9-epoxy-11,15-dihydroxy-15-[1-(4-fluorobutyl)cyclobutyl]-16,17,18,19,20-pentanorprosta-5,13-dienoic acid methyl ester stimulate uterine contraction in the pregnant female rat when administered intravenously on the 20th day of gestation at the doses of 10 and 10–20 μg/kg animal body weight, respectively.

Preferred PGI₂ analogues of the present invention are as follows: 18-chloro-19,20-dinor-PGI₂, 19-chloro-20-nor-PGI₂, 20-chloro-PGI₂, 15-methyl-20-chloro-PGI₂, 16-methyl-20-chloro-PGI₂, 17-methyl-20-chloro-PGI₂, 18-methyl-20-chloro-PGI₂, 19-methyl-20-chloro-PGI₂, 15,16-dimethyl-20-chloro-PGI₂, 16,16-dimethyl-20-chloro-PGI₂, 16,17-dimethyl-20-chloro-PGI₂, 16,19-dimethyl-20-chloro-PGI₂, 16-ethyl-20-chloro-PGI₂, 17-ethyl-20-chloro-PGI₂, 16-propyl-20-chloro-PGI₂, 17-propyl-20-chloro-PGI₂, 20-chloromethyl-PGI₂, 20-(2-chloroethyl)-PGI₂, 20-(3-chloropropyl)-PGI₂, 20-(4-chlorobutyl)-PGI₂, 15-[1-(3-chloropropyl)cyclobutyl]-16,17,18,19,20-pentanor-PGI₂, 15-[1-(4-chlorobutyl)cyclobutyl]-16,17,18,19,20-pentanor-PGI₂, 15-[1-(5-chloropentyl)cyclobutyl]-16,17,18,19,20-pentanor-PGI₂, 15-[1-(6-chlorohexyl)cyclobutyl]-16,17,18,19,20-pentanor-PGI₂, 15-(3-chloromethyl)cyclopentyl-16,17,18,19,20-pentanor-PGI₂, 15-[3-(2-chloroethyl)cyclopentyl]-16,17,18,19,20-pentanor-PGI₂, 15-[3-(3-chloropropyl)cyclopentyl]-16,17,18,19,20-pentanor-PGI₂, 15-[3-(4-chlorobutyl)cyclopentyl]-16,17,18,19,20-pentanor-PGI₂, 15-(3-chloromethyl)cyclohexyl-16,17,18,19,20-pentanor-PGI₂, 15-[3-(2-chloroethyl)cyclohexyl]-16,17,18,19,20-pentanor-PGI₂, 15-[3-(3-chloropropyl)cyclohexyl]-16,17,18,19,20-pentanor-PGI₂, 15-[3-(4-chlorobutyl)cyclohexyl]-16,17,18,19,20-pentanor-PGI₂, the corresponding compounds in which the chlorine atom is replaced by fluorine, and 13,14-dihydro analogues, esters, cyclodextrin clathrates and non-toxic salts of such chloro and fluoro compounds.

The most preferred PGI₂ analogues of the invention are (5Z,13E)-(9α,11α,15S,16RS)-6,9-epoxy-11,15-dihydroxy-16-methyl-20-chloroprosta-5,13-dienoic acid methyl ester, (5Z,13E)-(9α,11α,15R)-6,9-epoxy-11,15-dihydroxy-15-[1-(4-fluorobutyl)cyclobutyl]-16,17,18,19,20-pentanorprosta-5,13-dienoic acid methyl ester, (5Z,13E)-(9α,11α,15S,17R)-6,9-epoxy-11,15-dihydroxy-17-methyl-20-chloroprosta-5,13-dienoic acid methyl ester, (5Z,13E)-(9α,11α,15S)-6,9-epoxy-11,15-dihydroxy-15-[3-(2-chloroethyl)cyclopentyl]-16,17,18,19,20-pentanorprosta-5,13-dienoic acid methyl ester and (5Z,13E)-(9α,11α,15S)-6,9-epoxy-11,15-dihydroxy-20-chloroprosta-5,13-dienoic acid methyl ester.

The following Reference Example and Examples illustrate the preparation of prostaglandin I₂ analogues of the present invention. In them 'TLC', 'IR' and 'NMR' represent respectively 'Thin layer chromatography', 'Infrared absorption spectrum' and 'Nuclear magnetic resonance spectrum'. Where solvent ratios are specified in, e.g. chromatographic separations, the ratios are by volume.

REFERENCE EXAMPLE 1

(5Z,13E)-(9α,11α,15R)-9,11,15-Trihydroxy-15-[1-(4-fluorobutyl)cyclobutyl]-16,17,18,19,20-pentanorprosta-5,13-dienoic acid methyl ester To a solution of 1.4 g of (5Z,13E)-(9α,11α,15R)-9-hydroxy-11,15-bis-tetrahydropyran-2'-yloxy-15-[1-(4-fluorobutyl)cyclobutyl]-16,17,18,19,20-pentanorprosta-5,13-dienoic acid methyl ester [prepared as described in Example 10 of British Patent Application No. 29756/78 (published under the Serial No. 2002355 A)] in 3 ml of tetrahydrofuran was added 15 ml of a 65% (v/v) aqueous solution of acetic acid. The reaction mixture was stirred for 3 hours at 50° C. and then concentrated under reduced pressure to give an oily product containing acetic acid which was removed azeotropically with toluene under reduced pressure. The residue obtained was purified by column chromatography on silica gel using a mixture of cyclohexane and ethyl acetate (1:1) as eluant to give 645 mg of the title compound having the following physical characteristics:
TLC (developing solvent, ethyl acetate): Rf=0.26;
IR (liquid film): $\nu$=2950, 2880, 1745 cm$^{-1}$;
NMR (CDCl$_3$ solution): $\delta$=5.66–5.30 (4H, m), 4.70 (1H, t), 4.3–3.8 (4H, m), 3.67 (3H, s).

EXAMPLE 1

(13E)-(5RS,6RS,9α,11α,15S,16RS)-5-Iodo-6,9-epoxy-11,15-dihydroxy-16-methyl-20-chloroprost-13-enoic acid methyl ester Under an atmosphere of nitrogen, 194 mg of anhydrous potassium carbonate was added to a solution of 140 mg of (5Z,13E)-(9α,11α,15S,16RS)-9,11,15-trihydroxy-16-methyl-20-chloroprosta-5,13-dienoic acid methyl ester [prepared as described in Example 8 of British Patent Application No. 22090/75 and e.g. the equivalent Belgian Specification No. 842,113] in 5 ml of methylene chloride. To the reaction mixture was added 200 mg of iodine in portions during 2 hours with stirring at 0° C. The reaction mixture was diluted with diethyl ether, washed with an aqueous solution of sodium thiosulphate, water and an aqueous solution of sodium chloride, dried over anhydrous magnesium sulphate and concentrated under reduced pressure. The residue was purified by column chromatography on silica gel using a mixture of cyclohexane and ethyl acetate (2:1) as eluent to give 135 mg of the title compound having the following physical characteristics:
TLC (developing solvent, chloroform-tetrahydrofuran:acetic acid=10:2:1): Rf=0.44;
IR (liquid film): $\nu$=3400, 1740, 1440, 1250, 970 cm$^{-1}$;
NMR (CDCl$_3$ solution): $\delta$=5.7–5.4 (2H, m), 4.7–4.4 (1H, m), 4.25–3.7 (4H, m), 3.68 (3H, s), 3.55 (2H, t), 1.0–0.7 (3H, m).

The following compounds were prepared by the same procedure as described above.

(a) (13E)-(5RS,6RS,9α,11α,15R)-5-Iodo-6,9-epoxy-11,15-dihydroxy-15-[1-(4-fluorobutyl)cyclobutyl]-16,17,18,19,20-pentanorprost-13-enoic acid methyl ester, having the following physical characteristics, was prepared from (5Z,13E)-(9α,11α,15R)-9,11,15-trihydroxy-15-[1-(4-fluorobutyl)cyclobutyl]-16,17,18,19,20-pentanorprosta-5,13-dienoic acid methyl ester (prepared as described in Reference Example 1).
TLC (developing solvent, ethyl acetate): Rf=0.39;
IR (liquid film): $\nu$=2950, 2880, 1745 cm$^{-1}$;
NMR (CDCl$_3$ solution): $\delta$=5.63–5.33 (2H, m), 5.0–4.3 (3H, m), 3.57 (3H, s).

(b) (13E)-(5RS,6RS,9α,11α,15S,17R)-5-Iodo-6,9-epoxy-11,15-dihydroxy-17-methyl-20-chloroprost-13-enoic acid methyl ester, having the following physical characteristics, was prepared from (5Z,13E)-(9α,11α,15S,17R)-9,11,15-trihydroxy-17-methyl-20-chloroprosta-5,13-dienoic acid methyl ester:
IR (liquid film): $\nu$=3500, 3400 cm$^{-1}$;
NMR (CDCl$_3$ solution): $\delta$=5.63–5.43 (2H, m), 4.55 (1H, m), 4.10 (2H, m), 3.68 (3H, s), 3.53 (2H, t), 0.94 (3H, d).

(c) (13E)-(5RS,6RS,9α,11α,15S)-5-Iodo-6,9-epoxy-11,15-dihydroxy-15-[3-(2-chloroethyl)cyclopentyl]-16,17,18,19,20-pentanorprost-13-enoic acid methyl ester, having the following physical characteristics, was prepared from (5Z,13E)-(9α,11α,15S)-9,11,15-trihydroxy-15-[3-(2-chloroethyl)cyclopentyl]-16,17,18,19,20-pentanorprosta-5,13-dienoic acid methyl ester:
TLC (developing solvent, ethyl acetate): Rf=0.38;
IR (liquid film): $\nu$=3400, 1740, 975 cm$^{-1}$;
NMR (CDCl$_3$ solution): $\delta$=5.65–5.4 (2H, m), 4.7–4.4 (1H, m), 4.2–3.3 (6H, m), 3.67 (3H, s).

EXAMPLE 2

(5Z,13E)-(9α,11α,15S,16RS)-6,9-Epoxy-11,15-dihydroxy-16-methyl-20-chloroprosta-5,13-dienoic acid methyl ester (16RS-Methyl-20-chloro-PGI$_2$ methyl ester)

Under an atmosphere of nitrogen, a solution of 116 mg of (13E)-(5RS,6RS,9α,11α,15S,16RS)-5-iodo-6,9-epoxy-11,15-dihydroxy-16-methyl-20-chloroprost-13-enoic acid methyl ester (prepared as described in Example 1) and 0.4 ml of 1,5-diazabicyclo[5,4,0]undecene-5 (DBU) was stirred at room temperature for 18 hours, and then cooled to 0° C. To the reaction mixture were added 2 ml of 1 N hydrochloric acid and 2 ml of phosphate buffer solution (pH 6.86) with cooling to 0° C. The reaction mixture was extracted quickly with diethyl ether. The extract was dried over anhydrous magnesium sulphate and concentrated under reduced pressure. The residue was purified by column chromatography on Florisil (an activated magnesium silicate: "Florisil" is a registered Trade Mark of Florin Co.) using a mixture of ethyl acetate and n-hexane (1:1) containing 0.1% of triethylamine as eluent to give 52 mg of the title compound having the following physical characteristics:
TLC (developing solvent, diethyl ether:acetone=3:1 containing 0.1% of triethylamine, using a silica gel plate pretreated with a 5% (v/v) solution of triethylamine in diethyl ether): Rf=0.52;
IR (chloroform solution): $\nu$=3400, 1730, 1700, 970 cm$^{-1}$;
NMR (CDCl$_3$+benzene solution) $\delta$=5.7–5.4 (2H, m), 4.7–4.4 (1H, m), 4.3–3.6 (3H, m), 3.65 (3H, s), 3.53 (2H, t), 1.0–0.7 (3H, m).

The following compounds were prepared by the same procedure as described above.

(a) (5Z,13E)-(9α,11α,15R)-6,9-Epoxy-11,15-dihydroxy-15-[1-(4-fluorobutyl)cyclobutyl]-16,17,18,19,20-pentanorprosta-5,13-dienoic acid methyl ester {15-[1-(4-fluorobutyl)cyclobutyl]-16,17,18,19,20-pentanor-PGI$_2$ methyl ester}, having the following physical characteristics, was prepared from (13E)-(5RS,6RS,9α,11α,15R)-5-iodo-6,9-epoxy-11,15-dihydroxy-15-[1-(4-fluorobutyl)cyclobutyl]-16,17,18,19,20-pentanorprost-13-enoic acid methyl ester [prepared as described in Example 1 (a)]:

TLC (developing solvent, ethyl acetate containing 0.1% of triethylamine, using a silica gel plate pretreated with a 5% solution of triethylamine in diethyl ether): Rf=0.40;

IR (liquid film): $\nu=2950, 2870, 1740, 1700, 1440, 1380$ cm$^{-1}$;

NMR (CCl$_4$ solution): $\delta=5.51$ (2H, t), 4.62 (1H, t), 4.05 (1H, t), 4.7–3.2 (6H, m), 3.63 (3H, s).

(b) (5Z,13E)-(9α,11α,15S,17R)-6,9-Epoxy-11,15-dihydroxy-17-methyl-20-chloroprosta-5,13-dienoic acid methyl ester (17R-methyl-20-chloro-PGI$_2$ methyl ester), having the following physical characteristics, was prepared from (13E)-(5RS,6RS,9α,11α,15S,17R)-5-iodo-6,9-epoxy-11,15-dihydroxy-17-methyl-20-chloroprost-13-enoic acid methyl ester [prepared as described in Example 1 (b)]:

IR (liquid film): $\nu=3400, 1740$ cm$^{-1}$;

NMR (CDCl$_3$ solution): $\delta=5.50$–5.30 (2H, m), 4.50 (1H, m), 3.63 (3H, s), 3.48 (2H, t), 0.95 (3H, d).

(c) (5Z,13E)-(9α,11α,15S)-6,9-Epoxy-11,15-dihydroxy-15-[3-(2-chloroethyl)cyclopentyl]-16,17,18,19,20-pentanorprosta-5,13-dienoic acid methyl ester {15-[3-(2-chloroethyl)cyclypentyl]-16,17,18,19,20-pentanor-PGI$_2$ methyl ester}, having the following physical characteristics, was prepared from (13E)-(5RS,6RS,9α,11α,15S)-5-iodo-6,9-epoxy-11,15-dihydroxy-15-[3-(2-chloroethyl)cyclopentyl]-16,17,18,19,20-pentanorprost-13-enoic acid methyl ester [prepared as described in Example 1 (c)]:

TLC (developing solvent, diethyl ether:acetone=3:1, containing 0.1% of triethylamine, using a silica gel plate pretreated with a 5% solution of triethylamine in diethyl ether): Rf=0.4;

IR (chloroform solution) $\nu=3400, 1740, 1700, 980$ cm$^{-1}$;

NMR (CDCl$_3$+benzene solution): $\delta=5.7$–5.4 (2H, m), 4.7–4.45 (1H, m), 4.35–3.3 (5H, m), 3.65 (3H, s).

EXAMPLE 3

(13E)-(5RS,6RS,9α,11α,15S)-5-Bromo-6,9-epoxy-11,15-dihydroxy-20-chloroprost-13-enoic acid methyl ester Under an atmosphere of nitrogen, 85 mg of N-bromosuccinimide were added to a solution of 175 mg of (5Z,13E)-(9α,11α,15S)-9,11,15-trihydroxy-20-chloroprosta-5,13-dienoic acid methyl ester [prepared as described in Example 4 of British Patent Application No. 22090/75 and, e.g. the equivalent Belgian Specification No. 842113] in 3 ml of a mixture of chloroform and tetrahydrofuran (1:1) and the mixture was stirred at room temperature for 10 minutes. The reaction mixture was diluted with ethyl acetate and washed with an aqueous solution of sodium chloride, dried over anhydrous sodium sulphate and concentrated under reduced pressure. The residue was purified by column chromatography on silica gel using a mixture of cyclohexane and ethyl acetate (1:2) as eluent to give 165 mg of the title compound having the following physical characteristics:

TLC (developing solvent, ethyl acetate): Rf=0.55;
IR (liquid film): $\nu=3400, 1720, 980$ cm$^{-1}$;

NMR (CDCl$_3$ solution): $\delta=5.62$–5.45 (2H, m), 4.66–4.38 (1H, m), 3.68 (3H, s), 3.55 (2H, t), 2.75 (3H, s).

EXAMPLE 4

(5Z,13E)-(9α,11α,15S)-6,9-Epoxy-11,15-dihydroxy-20-chloroprosta-5,13-dienoic acid methyl ester (20-chloro-PGI$_2$ methyl ester)

Under an atmosphere of nitrogen, 0.1 ml of DBU was added to a solution of 50 mg of (13E)-(5RS,6RS,9α,11α,15S)-5-bromo-6,9-epoxy-11,15-dihydroxy-20-chloroprost-13-enoic acid methyl ester (prepared as described in Example 3) in 0.2 ml of toluene. The mixture was stirred at 50° C. for 1 hour, then at 70° C. for 1.5 hours and then cooled to 0° C. To the reaction mixture were added 0.5 ml of 1 N hydrochloric acid and 0.5 ml of phosphate buffer solution (pH 6.86) with cooling to 0° C. The reaction mixture was extracted quickly with diethyl ether. The extract was dried over anhydrous sodium sulphate and concentrated under reduced pressure. The residue was purified by column chromatography on Florisil using a mixture of ethyl acetate and n-hexane (1:1) containing 0.1% of triethylamine as eluent to give 15 mg of the title compound having the following physical characteristics:

TLC (developing solvent, diethyl ether:acetone=3:1, containing 0.1% of triethylamine, using a silica gel plate pretreated with a 5% (v/v) solution of triethylamine in diethyl ether): Rf=0.52;

IR (liquid film): $\nu=3400, 1740, 1700, 980$ cm$^{-1}$;

NMR (CDCl$_3$ solution): $\delta=5.61$–5.40 (2H, m), 4.69–4.47 (1H, m), 4.24–3.90 (2H, m), 3.66 (3H, s), 3.62 (1H, d), 3.53 (2H, t), 2.33 (2H, t).

The present invention includes within its scope pharmaceutical compositions which comprise at least one new therapeutically useful compound of general formula II, or cyclodextrin clathrate thereof or, when R$^1$ in formula II represents a hydrogen atom, non-toxic salt thereof or, when R$^1$ represents a group

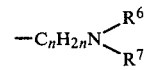

in which n, R$^6$ and R$^7$ are as hereinbefore defined, non-toxic acid addition salt thereof, together with a pharmaceutical carrier or coating. In clinical practice the new compounds of the present invention will normally be administered parenterally, vaginally or rectally.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

Solid compositions for vaginal administration include pessaries formulated in manner known per se and containing one or more of the active compounds.

Solid compositions for rectal administration include suppositories formulated in manner known per se and containing one or more of the active compounds.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection. The dose employed depends upon the desired therapeutic effect, the route of administration and the duration of the treatment.

In the human adult, each dose per person is generally between 0.05 and 500 μg by parenteral administration in the treatment of hypertension, between 0.05 and 500 μg by parenteral administration in the treatment of disorders of the peripheral circulation, and between 0.05 and 500 μg by parenteral administration in the prevention and treatment of cerebral thrombosis, myocardial infarction and arteriosclerosis.

The following Example illustrates pharmaceutical compositions according to the invention.

EXAMPLE 5

(5Z,13E)-(9α,11α,15S,16RS)-6,9-Epoxy-11,15-dihydroxy-16-methyl-20-chloroprosta-5,13-dienoic acid methyl ester (500 μg) was dissolved in ethanol (5 ml). The solution was then sterilized by passage through a bacteria-retaining filter and placed in 0.1 ml portions in 1 ml ampoules, to give 10 μg of (5Z,13E)-(9α,1-1α,15S,16RS)-6,9-epoxy-11,15-dihydroxy-16-methyl-20-chloroprosta-5,13-dienoic acid methyl ester per ampoule. The ampoules were sealed. The contents of an ampoule diluted to a suitable volume, e.g. with 1 ml of tris-HCl-buffer solution (pH 8.6), gave a solution ready for administration by injection.

We claim:

1. A prostaglandin $I_2$ analogue of the formula:

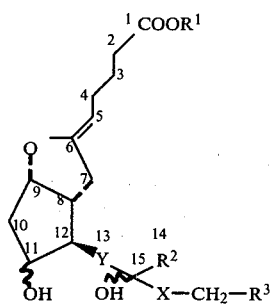

II wherein Y represents ethylene or trans-vinylene, $R^1$ represents a hydrogen atom, a straight- or branched-chain alkyl group containing from 1 to 12 carbon atoms, an aralkyl group containing from 7 to 12 carbon atoms, a cycloalkyl group containing from 4 to 7 carbon atoms unsubstituted or substituted by at least one straight- or branched-chain alkyl group containing from 1 to 4 carbon atoms, a phenyl group unsubstituted or substituted by at least one chlorine atom, trifluoromethyl group, straight- or branched-chain alkyl group containing from 1 to 4 carbon atoms or phenyl group, a $-C_mH_{2-m}COOR^4$ group, wherein m represents an integer of from 1 to 12 and $R^4$ represents a straight- or branched-chain alkyl group containing from 1 to 4 carbon atoms, a $-C_nH_{2n}OR^5$ group, wherein n represents an integer of from 2 to 12 and $R^5$ represents a hydrogen atom or a straight- or branched-chain alkyl group containing from 1 to 4 carbon atoms, or a

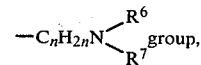

wherein n is as hereinbefore defined and $R^6$ and $R^7$, which may be the same or different, each represent a straight- or branched-chain alkyl group containing from 1 to 4 carbon atoms, $R^2$ represents a hydrogen atom or a methyl or ethyl group, X represents a straight or branched chain $-C_pH_{2p}-$ group, wherein p represents an integer of from 2 to 8, or a

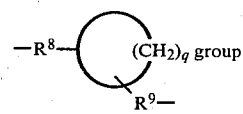

wherein $R^8$ represents a single bond, or a straight- or branched-chain alkylene group containing from 1 to 4 carbon atoms, $R^9$ represents a single bond or a straight- or branched-chain alkylene group containing from 1 to 8 carbon atoms, and q represents an integer of from 3 to 6, $R^3$ represents a chlorine or fluorine atom, the wavy line attached to the carbon atoms in positions 11 and 15 represents α- or β-configuration or mixtures thereof, and the double bond between $C_5-C_6$ is in the Z configuration, cyclodextrin clathrates thereof, and, when $R^1$ represents a hydrogen atom, non-toxic salts thereof and, when $R^1$ represents a

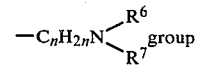

in which n, $R^6$ and $R^7$ are as hereinbefore defined, non-toxic acid addition salts thereof.

2. A prostaglandin analogue according to claim 1 wherein $R^1$ represents a straight- or branched-chain alkyl group containing from 1 to 4 carbon atoms.

3. A prostaglandin analogue according to claim 1 wherein $R^1$ represents methyl.

4. A prostaglandin analogue according to claim 1 wherein $R^2$ represents a hydrogen atom.

5. A prostaglandin analogue according to claim 1 wherein Y represents trans-vinylene.

6. A prostaglandin analogue according to claim 1 wherein X represents a $-C_pH_{2p}-$ group wherein p is as defined in claim 1.

7. A prostaglandin analogue according to claim 6 wherein the $-C_pH_{2p}-$ group is a tetramethylene group unsubstituted or substituted by a methyl group.

8. A prostaglandin analogue according to claim 1 wherein X represents a

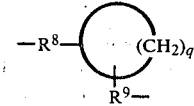

wherein $R^8$ represents a single bond or a straight- or branched-chain alkylene group containing from 1 to 4 carbon atoms, $R^9$ represents a single bond or a straight- or branched-chain alkylene group containing from 1 to 8 carbon atoms and q represents an integer of from 3 to 6.

9. A prostaglandin analogue according to claim 8 wherein $R^8$ represents a single bond.

10. A prostaglandin analogue according to claim 8 wherein q represents 3 or 4.

11. A prostaglandin analogue according to claim 8 wherein $R^9$ represents a straight-chain alkylene group containing from 1 to 3 carbon atoms.

12. A prostaglandin analogue according to claim 1 wherein the hydroxy groups attached to the C-11 and C-15 carbon atoms in general formula II depicted in claim 1 are in α-configuration.

13. A prostaglandin analogue according to claim 1 which is (5Z,13E)-(9α,11α,15S,16RS)-6,9-epoxy-11,15-dihydroxy-16-methyl-20-chloroprosta-5,13-dienoic acid methyl ester and cyclodextrin clathrates thereof.

14. A prostaglandin analogue according to claim 1 which is (5Z,13E)-(9α,11α,15R)-6,9-epoxy-11,15-dihydroxy-15-[1-(4-fluorobutyl)cyclobutyl]-16,17,18,19,20-pentanorprosta-5,13-dienoic acid methyl ester and cyclodextrin clathrates thereof.

15. A prostaglandin analogue according to claim 1 which is (5Z,13E)-(9α,11α,15S,17R)-6,9-epoxy-11,15-dihydroxy-17-methyl-20-chloroprosta-5,13-dienoic acid methyl ester and cyclodextrin clathrates thereof.

16. A prostaglandin analogue according to claim 1 which is (5Z,13E)-(9α,11α,15S)-6,9-epoxy-11,15-dihydroxy-15-[3-(2-chloroethyl)cyclopentyl]-16,17,18,19,20-pentanorprosta-5,13-dienoic acid methyl ester and cyclodextrin clathrates thereof.

17. A prostaglandin analogue according to claim 1 which is (5Z,13E)-(9α,11α,15S)-6,9-epoxy-11,15-dihydroxy-20-chloroprosta-5,13-dienoic acid methyl ester and cyclodextrin clathrates thereof.

18. A pharmaceutical composition useful in the treatment of hypertension, in the treatment of disorders of the peripheral circulation, in the prevention and treatment of cerebral thrombosis, myocarbial infarction and arteriosclerosis, which comprises, as active ingredient, an effective amount of at least one prostaglandin analogue as claimed in any one of claims 1 or 2 to 17, or a cyclodextriin clathrate thereof or, when $R^1$ in general formula II represents a hydrogen atom, a non-toxic salt thereof or, when $R^1$ in general formula II depicted in claim 1 represents a

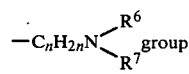

in which n, $R_6$ and $R^7$ are as defined in claim 1, a non-toxic acid addition salt thereof, in association with a pharmaceutical carrier or coating.

19. A compound of the formula:

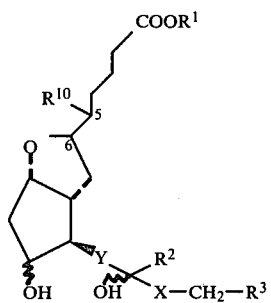

wherein $R^{10}$ represents a bromine or iodine atom and the other symbols are as defined in claim 1.

* * * * *